Figure 1:
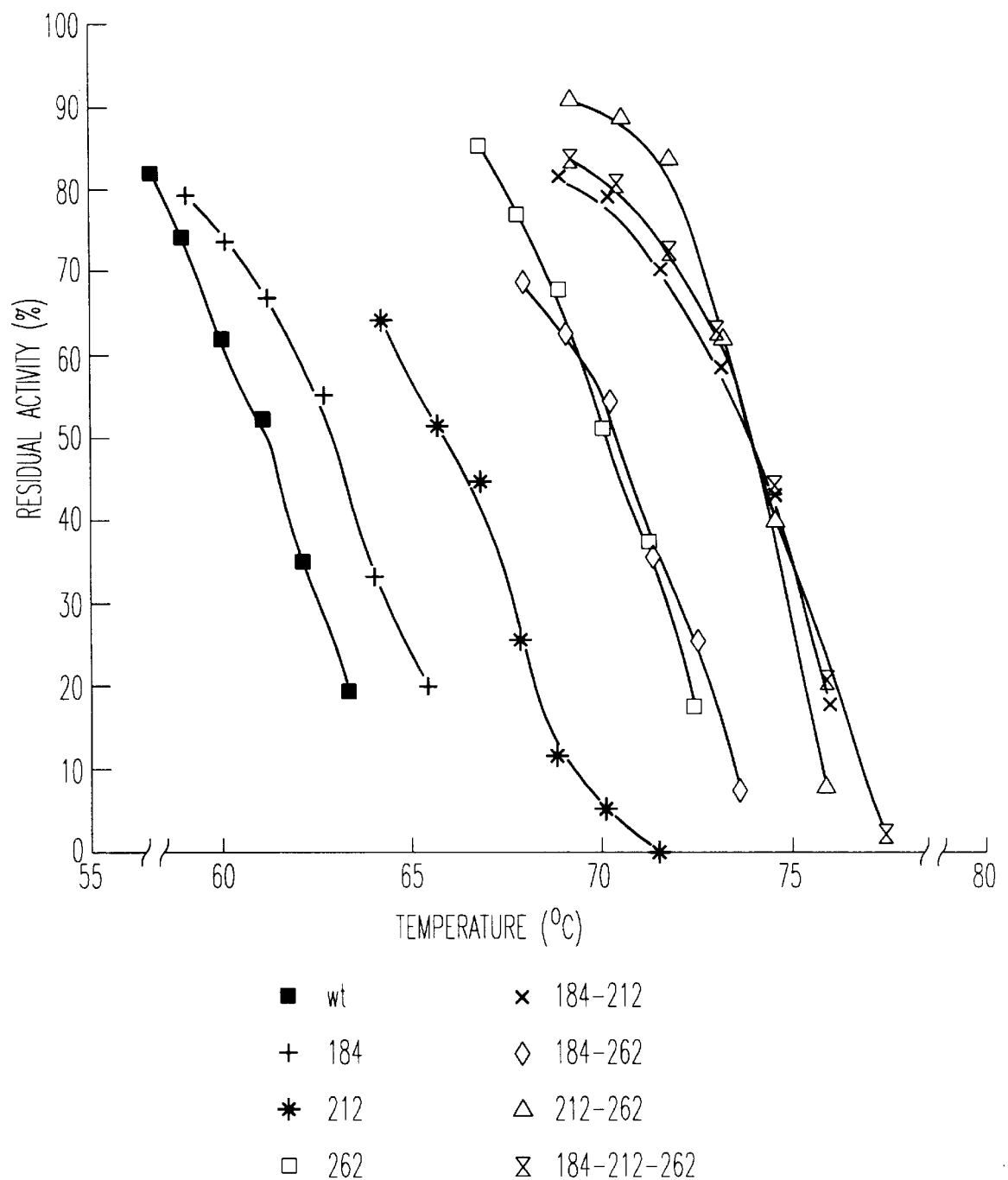

United States Patent [19]
Grifantini et al.

[11] Patent Number: 5,877,002
[45] Date of Patent: Mar. 2, 1999

[54] THERMOSTABLE MUTANTS OF D-N-α-CARBAMOYLASE

[75] Inventors: Renata Grifantini, Milan; Giovanna Carpani, Sergnano; Giuliano Galli, Milan; Guido Grandi, Segrate, all of Italy

[73] Assignee: Eniricerche S.p.A., Milan, Italy

[21] Appl. No.: 762,433

[22] Filed: Dec. 9, 1996

[30] Foreign Application Priority Data

Dec. 21, 1995 [IT] Italy .............................. MI95 A 002700

[51] Int. Cl.⁶ ...................................................... C12N 9/80
[52] U.S. Cl. ............................................. 435/228; 435/227
[58] Field of Search ...................................... 435/227, 228

[56] References Cited

U.S. PATENT DOCUMENTS 4,312,948  1/1982  Olivieri et al. ........................ 435/106
4,980,284  12/1990  Makryaleas et al. .................... 435/106

FOREIGN PATENT DOCUMENTS 0 610 517   8/1994  European Pat. Off. .
0 677 585  10/1995  European Pat. Off. .
   677584  10/1995  European Pat. Off. .

OTHER PUBLICATIONS

Buson et al., FEMS Microbiol. Lett. 145:55–62, 1996.

Primary Examiner—Eric Grimes
Attorney, Agent, or Firm—Oblon, Spivak, McClelland, Maier & Neustadt, P.C.

[57] ABSTRACT

The present invention relates to thermostable mutants of *Agrobacterium radiobacter* D-N-α-carbamoylase and means and methods for their preparation. The thermostable mutants have an unaltered or improved activity with respect to the wild-type enzyme and are particularly useful in the preparation of D-α-amino acids.

7 Claims, 2 Drawing Sheets

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 304 amino acids
        ( B ) TYPE: amino acid
        ( D ) TOPOLOGY: linear ( x i ) SEQUENCE DESCRIPTION: SEQ ID NO:1:

```
Met Thr Arg Gln Met Ile Leu Ala Val Gly Gln Gln Gly Pro Ile Ala
1               5                   10                  15
Arg Ala Glu Thr Arg Glu Gln Val Val Gly Arg Leu Leu Asp Met Leu
                20                  25                  30
Thr Asn Ala Ala Ser Arg Gly Val Asn Phe Ile Val Phe Pro Glu Leu
            35                  40                  45
Ala Leu Thr Thr Phe Phe Pro Arg Trp His Phe Thr Asp Glu Ala Glu
        50              55                  60
Leu Asp Ser Phe Tyr Glu Thr Glu Met Pro Gly Pro Val Val Arg Pro
65                  70                  75                  80
Leu Phe Glu Thr Ala Ala Glu Leu Gly Ile Gly Phe Asn Leu Gly Tyr
                85                  90                  95
Ala Glu Leu Val Val Glu Gly Gly Val Lys Arg Arg Phe Asn Thr Ser
                100                 105                 110
Ile Leu Val Asp Lys Ser Gly Lys Ile Val Gly Lys Tyr Arg Lys Ile
                115                 120                 125
His Leu Pro Gly His Lys Glu Tyr Glu Ala Tyr Arg Pro Phe Gln His
        130                 135                 140
Leu Glu Lys Arg Tyr Phe Glu Pro Gly Asp Leu Gly Phe Pro Val Tyr
145                 150                 155                 160
Asp Val Asp Ala Ala Lys Met Gly Met Phe Ile Cys Asn Asp Arg Arg
                165                 170                 175
Trp Pro Glu Thr Trp Arg Val Met Gly Leu Lys Gly Ala Glu Ile Ile
                180                 185                 190
Cys Gly Gly Tyr Asn Thr Pro Thr His Asn Pro Pro Val Pro Gln His
        195                 200                 205
Asp His Leu Thr Ser Phe His His Leu Leu Ser Met Gln Ala Gly Ser
        210                 215                 220
Tyr Gln Asn Gly Ala Trp Ser Ala Ala Ala Gly Lys Val Gly Met Glu
225                 230                 235                 240
Glu Gly Cys Met Leu Leu Gly His Ser Cys Ile Val Ala Pro Thr Gly
                245                 250                 255
Glu Ile Val Ala Leu Thr Thr Thr Leu Glu Asp Glu Val Ile Thr Ala
                260                 265                 270
Ala Val Asp Leu Asp Arg Cys Arg Glu Leu Arg Glu His Ile Phe Asn
        275                 280                 285
Phe Lys Ala His Arg Gln Pro Gln His Tyr Gly Leu Ile Ala Glu Phe
        290                 295                 300
```

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CTCGGCTTCC CGGTCTATGA CGTCGAC        27

( 2 ) INFORMATION FOR SEQ ID NO:3:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

GGCTTACTTG TCTGCTTTC   19

( 2 ) INFORMATION FOR SEQ ID NO:4:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

AACGATCGCC GCTGGCCT   18

( 2 ) INFORMATION FOR SEQ ID NO:5:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

CCCAAGCTTT AATGATGATG ATGATGATGG CCACCAAATT CCGCGAT   47

( 2 ) INFORMATION FOR SEQ ID NO:6:

( i ) SEQUENCE CHARACTERISTICS:
    ( A ) LENGTH: 8 amino acids
    ( B ) TYPE: amino acid
    ( D ) TOPOLOGY: linear ( x i ) SEQUENCE DESCRIPTION: SEQ ID NO:6:

His His His His His His Gly Gly
1       5

( 2 ) INFORMATION FOR SEQ ID NO:7:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

CTCGGCTTCC CGGTCTATGA CGTCGAC   27

( 2 ) INFORMATION FOR SEQ ID NO:8:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

GGCTTACTTG TCTGCTTTC   19

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GCCCTTAAGT CCCAACACCC GCCACGT 27

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GTGGTGGAAG GACGCCAGAT GGTCGTG 27

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TTCCAACGTC GTGGCCAGGG CAACGAT 27

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

AAGCTTCAAA TTTCCGCGAT CAG 23

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GTCGGTGAAA TACCACCGCG GGAA 24

( 2 ) INFORMATION FOR SEQ ID NO:14:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CGTCAGATGA TCATGCTGGG GAACTTCGGG ATTGTG 36

( 2 ) INFORMATION FOR SEQ ID NO:15:

(  i  ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

CAGCATGCAT  CCCTCCTCCA  TGCCAGCCTT  GCCGCC                              36

THERMOSTABLE MUTANTS OF D-N-α-CARBAMOYLASE

The present invention relates to thermostable mutants of D-N-α-carbamoylase, means and methods for their preparation and their use in the production of D-α-aminoacids.

D-α-aminoacids are important intermediates in the preparation of pharmacologically active substances, pesticides and sweeteners. For example, D-phenylglycine and D-para-hydroxyphenylglycine are used in the synthesis of semi-synthetic penicillins and cephalosporins, whereas D-valine is used in the preparation of the insecticide fluvanylate and D-alanine in the production of sweeteners.

The preparation of D-α-aminoacids starting from racemic mixtures of their N-carbamoyl derivatives or racemic mixtures of their corresponding 5-substituted hydantoins by chemical or enzymatic hydrolysis, is known in the art.

Chemical processes however, which are generally based on the use of camphosulfonic acid, have disadvantages deriving from the complex procedures required for the resolution and purification of D-α-aminoacids. As a result these processes are economically of little interest from an industrial point of view.

On the other hand, processes using enzymes or enzymatic systems obtained from microorganisms (EP-199.943, EP-309.310, U.S. Pat. No. 4,312,948, FR 2456728) have limitations due not only to the high production and purification costs of these enzymes, but also to their instability which, as is known, can be attributed to a series of factors such as for example thermal denaturation, oxidative phenomena and aggregrations caused by bonds of the hydrophobic and/or covalent type.

Identifying the causes of these instabilities is therefore of utmost importance in finding solutions for improving and making an enzymatic process more competitive. It is often difficult however to be able to accurately identify (i) the causes of this instability and (ii) possible remedies for eliminating or reducing the instability without altering the activity of the enzyme.

The term enzymatic system refers to a system consisting of D-hydantoinase and D-carbamoylase enzymes which transform, respectively, D-hydantoins into D-carbamoyl derivatives and the latter into D-aminoacids.

D-N-α-carbamoylase has a lower stability to hydantoinase under the operating conditions used for the production process of D-α-aminoacids.

Mutants of D-N-α-carbamoylase with an improved stability have been obtained as described in patent application EP-A-677584.

It is evident that a more stable carbamoylase at high temperatures allows the conversion rate of the substrate into the corresponding amino acids to be improved resulting in a considerable reduction in the production costs.

For example patent application EP-610517 describes thermostable mutants of D,N-α-carbamoylase obtained by one or more substitutions of amino acid residues in well determined sites. The more thermostable mutants however with the same catalytic biomass have a reduced activity with respect to the mutants of the present invention.

Figure 2:
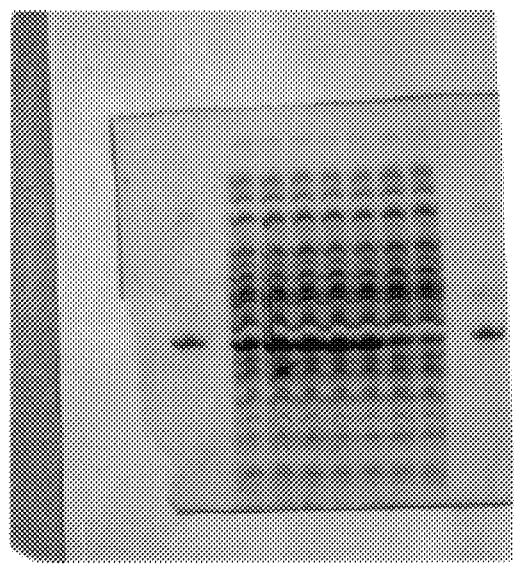

FIG. 1 shows the temperature inactivation curves of wild-type and mutant carbamoylases; and FIG. 2 shows cell extracts from cells expressing wild-type and mutant carbamoylases.

It has now been found that it is possible to obtain thermostable mutants of D-N-α-carbamoylase with an unaltered or improved enzymatic activity with respect to the wild type enzyme by the substitution of one or more residues in well determined sites of the amino acid sequence.

With these mutants it is possible to operate at higher temperatures than those at present used in a conventional process for the production of D-α-aminoacids, thus increasing the racemization rate of the isomer L, the solubility and the hydrolysis rate of the substrate. This consequently allows a reduction in the quantity of biomass and the time necessary for obtaining the complete conversion of the substrate into the corresponding D-α-aminoacids.

In accordance with this a first aspect of the present invention relates to thermostable mutants of D-N-α-carbamoylase characterized in that at least one of the amino acid residues in position 184, 212, 262 and 304 is substituted with a different residue selected from the group of natural amino acids. The amino acid sequence of the wild-type Agrobacterium radiobacter D-N-α-carbamoylase is given in SEQ ID NO:1.

Another object of the present invention relates to a nucleotide sequence which encodes at least one mutant of D-N-α-carbamoylase with an improved thermal stability.

A further object of the present invention relates to a replicative recombinant expression vector comprising said sequence.

Another object of the present invention relates to a microorganism transformed with said vector.

The present invention also relates to a process for the preparation of at least one mutant of D-N-α-carbamoylase with an improved thermal stability which comprises breeding under suitable conditions a transformed microorganism and separating the mutant thus obtained.

A further object of the present invention relates to the use of these transformed microorganisms or of a mutant of D-N-α-carbamoylase obtained from said microorganism in a process for the production of D-a-amino acids. Further objects of the present invention will appear evident from the description and following examples.

The mutants of D-N-α-carbamoylase of the present invention are characterized in that at least one of the residues in position 184, 212, 262 and 304 of the amino acid sequence of the wild type enzyme is substituted with a different residue selected from L-alanine, L-serine, L-lysine, L-arginine, L-aspartic acid, L-glutamic acid, L-asparagine, L-glutamine, L-histidine, L-glycine, L-leucine, L-isoluecine, L-valine, L-tyrosine, L-threonine, L-tryptophan, L-phenylalanine, L-methionine or L-proline.

The preferred mutants of the present invention are those of D-N-α-carbamoylase in which the residue Met 184 is substituted with L-leucine (Leu), the residues Thr212 and Thr262 with L-alanine (Ala) and the residue Phe304 with L-isoleucine (Ile).

Particularly preferred mutants of the present invention are those of D-N-α-carbamoylase in which at least two of the amino acid residues in positions 184, 212, 262 and 304 are substituted.

The mutants of D-N-α-carbamoylase of the present invention can be prepared with a process which comprises:

a) introducing one or more mutations in the gene which encodes D-N-α-carbamoylase;

b) cloning the mutagenized gene obtained in step a) in a cloning vector;

c) transforming a host strain with the recombinant vector obtained in step b);

d) culturing in a suitable culture medium the host strain transformed as in step c); and finally e) separating and purifying the mutant of D-N-α-carbamoylase thus obtained.

As far as the D-N-α-carbamoylase gene to be mutagenized is concerned, this can be isolated from microorganisms such as Pseudomonas, Hansenula, Agrobacterium, Aerobacter, Aeromonas, Bacillus, Moraxella, Brevibacterium, Flavobacterium, Serratia, Micrococcus, Arthrobacter or paracoccus. Specific examples of these microorganisms are *Bacillus macroides* ATCC 12905, *Aerobacter cloacae* IAM 1221, Agrobacterium sp. IP I-671, *Agrobacterium radiobacter* NRRLB 11291, Pseudomonas sp. FERM BP 1900. According to one embodiment of the present invention the gene isolated from *Agrobacterium radiobacter* NRRLB 11291 was mutagenized.

The introduction of a mutation in the gene can be carried out with one of the known mutagenesis techniques in vitro such as for example specific-site mutagenesis or, preferably random mutagenesis. The latter can be carried out using the PCR technique (Polymerase chain reaction) according to the indications provided by Leung D. W. et al., 1989, Technique, 1, 11–15 and which can be thus schematized:

(1) synthesis of two oligonucleotides (forward and reverse) upstream and downstream to the fragment to be amplified; and (2) amplification of the fragment under conditions in which the polymerase enzyme inserts, with a frequence of about 1–2%, bases not complementary to the template used.

According to an embodiment of the present invention the gene of D-N-α-carbamoylase fused at the 3'-end to a sequence which encodes a tail of polyhistidine (poly-his), was subjected to random mutagenesis to allow possible purification by means of the IMAC technique (Immobilized Metal Ion Affinity Chromatography) and contemporaneous immobilization on a solid carrier.

In particular the following pair of oligonucleotides was used for the amplification:

a) 5'CTC GGC TTC CCG GTC TAT GAC GTC GAC3' (forward) (SEQ ID NO:2)

b) 5'GGC TTA CTT GTC TGC TTT C 3' (reverse) (SEQ ID NO:3).

The oligonucleotides can be synthesized with the known methods using any of the equipment available on the market.

The amplification product, after cutting with suitable restriction enzymes was purified and ligated to a vector digested with the same restriction enzymes. The ligase reaction can be carried out using conventional methods in the presence of the T4 DNA ligase enzyme.

The ligase mixture was then used to transform host cells, preferably *E.coli*, made competent for example by electroporation (Dower W. J., Miller J. F. and Ragsdale C. W., N. A. R. (1988), 16, 6127) and the transformants were cultured on a suitable culture medium in the presence of an antibiotic.

The selection of the clones containing thermostabilizing mutations was carried out by making replicas from each transformation plate on a nitrocellulose membrane (MFS, Sartorius). These replicas were subjected to freezing-defreezing cycles in order to lyse the colonies and were then put at 48.5° C. for 16 hours. After this inactivation treatment the membranes were transferred onto plates containing as substrate the carbamoyl of a D-amino acid, buffer sodium-phosphate pH 7, agarose (BioRad) and red phenol and incubated at 37–40° C. After a few hours the colonies had a red-violet colouring, whereas the wild-type colonies no longer had any activity.

Various thermostable clones were isolated with this screening. The plasmid DNA extracted from these clones was then sequenced to identify on a DNA level the mutations introduced by random mutagenesis.

The analysis of the sequence can be carried out using known techniques based on Sanger's enzymatic method (Sanger, F. & Coulson, A. R., (1975), *J. Mol. Biol.*, 94, 441–443).

The following mutations were identified for each clone: Met184→Leu, Thr212→Ala, Thr262→Ala and Phe304→Ile.

Once the thermostabilizing mutations had been identified, they were introduced into the carbamoylase gene without the Poly-His tail. The introduction of a mutation in well-determined sites of the gene can be carried out using one of the known mutagenesis techniques in vitro. Among the various methods which produce specific modifications on a DNA sequence, the most well-known are those which use synthetic single-stranded oligonucleotides.

In particular a modification of the method described by Zoller, M. J. and Smith, M., (1982), Nucl.-Acid. Res., 10, 6487–6500), was used which comprises:

1) inserting the gene of D-N-α-carbamoylase or part of this (target sequence) into a bacteriophage of the type M13 or into a plasmid deriving therefrom and preparing it in a single strand form which can be used as a "mould" (template) for the synthesis of the mutated product.

2) synthesizing an oligonucleotide complementary to the sequence to be mutagenized with the exception of an internal portion which determines the mutation;

3) annealing the synthetic oligonucleotide to the "mould". It will act as "primer" for the synthesis of the second modified strand;

4) reconstructing, by means of a polymerization and ligation passage in vitro, the double-stranded circular structure, of which one strand is the parental one, whereas the other brings the desired mutation;

5) eliminating the parental strand and reforming, by means of a polymerization and ligation passage in vitro, the double-stranded circular structure in which both the strands contain the desired mutation;

6) using the double-stranded form to transform competent host cells obtaining a population of mutant and wild-type clones; and finally 7) selecting the mutant clones.

Operating as described above, single and multiple mutants of D-N-α-carbamoylase were constructed, in which the residues in position 184, 212, 262 and 304 of the amino acid sequence of the wild-type enzyme were substituted with a different residue.

In accordance with the present invention the gene mutagenized as described above can be introduced into a cloning vector by correctly positioning the gene under the control of sequences which regulate its expression in the host strain. Vectors which are suitable for the purpose can be selected from plasmids, bacteriophages and cosmids available on the market or at authorized collection centres.

A non-limiting example of vectors suitable for the purposes of the present invention is the plasmid pSM671 CBS 205.94.

To verify the activity and thermostability characteristics of the mutants of the present invention, cells of *E.coli* transformed with a vector containing the gene mutagenized as described above were cultured in a suitable medium, at 37° C. for 16 hours. The protein extracts obtained from the cellular lysates were then analyzed by SDS-PAGE (electrophoresis on polyacrylamide gel containing sodiumdodecylsulfate). The results showed that the mutants were expressed in a soluble form and in comparable quantities with respect to each other and to the expression level of the wild-type enzyme. The activity test carried out on the raw extracts, as described by Weatherburn, M. W., (1967), (Anal. Chem., 39: 971), showed for all the mutants an activity which was comparable to or better than that of the wild-type enzyme.

Stability studies carried out at temperatures of between 50 and 80° C. for 30 minutes showed for the mutants tested a higher thermal stability than that of the wild-type D-N-α-carbamoylase.

According to another embodiment of the present invention the mutagenized gene of D-N-α-carbamoylase can be linked in tandem with the hydantoinase gene to construct expression operon systems regulated by a single promoter.

The recombinant vectors, containing the mutagenized D-N-α-carbamoylase gene or mutagenized hydantoinase-carbamoylase operon, can be introduced into a host microorganism selected from *B.subtilis* or *E.coli*.

These microorganisms are then cultured under aerobic conditions, in an aqueous medium containing assimilable sources of carbon and nitrogen as well as various cations, anions and, optionally, traces of vitamins, such as biotin or thiamine, or of amino acids.

Assimilable carbon sources comprise carbohydrates such as glucose, hydrolyzed starches, molasses, sucrose or other conventional carbon sources.

Examples of nitrogen sources can be selected, for example, from mineral salts of ammonium, such as ammonium nitrate, ammonium sulfate, ammonium chloride or ammonium carbonate and urea or materials containing organic or inorganic nitrogen such as peptone, yeast extract or meat extract.

The following cations and anions are equally suitable for the purposes of the present invention: potassium, sodium, magnesium, iron, calcium, acid phosphates, sulfates, chlorides, manganese, and nitrates.

The fermentation is carried out, under stirring, at a temperature of between 25° C. and 40° C., at a pH of between 6 and 7.5, preferably between 6.5 and 7.0.

The cells (biomass) recovered from the culture medium with conventional techniques such as centrifugation or filtration are used in the production of D-α-amino acids by conversion of racemic mixtures of N-carbamoyl amino acids or, when the cells express hydantoinase and modified carbamoylase enzymes, of racemic mixtures of 5-substituted hydantoins.

Alternatively it is possible to use the cellular extract obtained from the disintegration of the cells by sonication or French-press, or purified or partially purified enzymes or enzymes immobilized on insoluble solid carriers.

The purification can be carried out using one of the conventional techniques such as for example ionic exchange chromatography, gel filtration, hydrophobic chromatography or affinity chromatography such as IMAC (Immobilized Metal Ion Affinity Chromatography).

Examples of solid carriers suitable for the immobilization of the enzymes of the present invention can be products already activated available on the market such as for example Eupergit®C, Sepharosio® activated with BrCN, etc.

According to an embodiment of the present invention the mutants fused to a tail of polyhistidine can be purified and contemporaneously immobilized by means of the IMAC technique.

Numerous D-N-α-carbamoyl amino acids and hydantoins substituted in position 5 can be used in the process of the present invention. Possible substitutes in position 5 are selected from a linear or branched alkyl group with from 1 to 6 carbon atoms, which can be mono or polysubstituted with hydroxylic, carboxylic, sulfhydrylic or aminic groups or a phenyl or benzyl group which, in turn, can contain one or more substitutes in ortho, meta or para position.

Examples of 5-substituted hydantoins are: D,L-5-phenylhydantoin; D,L-5-para-hydroxyphenylhydantoin; D,L-5-methylhydantoin; D,L-5-isopropylhydantoin, D,L-5-tienylhydantoin; D,L-5-para-methoxyphenylhydantoin; D,L-5-p-chorophenyl-hydantoin; D,L-5-benzylhydantoin.

The conversion reaction of the starting substrate (5-substituted hydantoins or D-N-α-carbamoyl amino acids) into the corresponding D-α-amino acids is preferably carried out in a nitrogen atmosphere in hermetically closed equipment, at a temperature of between 25° and 70° C.

The pH of the reaction medium is maintained within values of between 6 and 10 and preferably between 7 and 8.5. This regulation of the pH can be carried out, for example, by the addition of a basic aqueous solution such as an aqueous solution of ammonia, potassium hydroxide, sodium hydroxide, sodium or potassium carbonate.

The initial concentration of the substrate is generally between 2% and 30% by weight.

The quantity of biomass or enzyme which is added to the reaction mixture will depend on the particular affinity of the substrate towards the enzymes. In general, a weight ratio biomass/substrate of between 1/1 and 1/50 can be used.

The D-α-amino acids prepared with the process of the present invention can be recovered from the reaction environment with classical methods such as ion exchange chromatography or precipitation of the amino-acid at its isoelectric point.

Although the invention relates to the production of mutants of D-N-α-carbamoylase of *A.radiobacter*, it is evident that it can be applied to the modification of homologous enzymes obtained from other microorganims.

In accordance with the present invention the plasmids pSM754, pSM755, pSM756 and pSM769 were deposited at the Centraalbureau Voor Schimmelcultures, SK Baarn (Holland) as respectively *E.coli* SMC341, SMC342, SMC343 and SMC355 where they received the deposit numbers CBS 665.95, CBS666.95, CBS 667.95 and CBS 758.95 respectively.

The following experimental examples provide a better illustration of the present invention but do not limit its scope.

EXAMPLE 1

Insertion of the polyHis tail into the gene of D-N-α-carbamoylase

The nucleotide sequence which encodes the polyHis tail was introduced into the D-N-α-carbamoylase gene by the amplification of a region of about 420 base pairs (bp) containing the 3'-end of the D-N-α-carbamoylase gene.

For this purpose the Polymerase Chain Reaction (PCR) technique was used using the following pair of oligonucleotides as primers:

a) 5'AAC GAT CGC CGC TGG CCT 3'  (FORWARD)   (SEQ ID no: 4)
   HindIII                                    BalI b) 5'CC CAA GCT TTA ATG ATG ATG ATG ATG ATG GCC ACC
              His  His His His His His Gly Gly   (SEQ ID no: 6)

AAA TTC CGC GAT 3'  (REVERSE)  (SEQ ID no: 5)

The oligonucleotide b) introduced the restriction site BalI useful for the selection of the transformants. The oligonucleotides are synthesized by the known methods using the DNA Synthesizer ® Oligo 1000 (Beckman).

The amplification was carried out in a DNA Thermal Cycler ® 480 (Perkin-Elmer Cetus) using a reaction mixture (100 µl) containing:

1 ng of the plasmid pSM637;

2.5 units of Taq polymerase (Boehringer);

10 mM Tris-HCl pH 8.3;

1.5 mM $MgCl_2$;

50 mM KCl, 0.01% (weight/volume) gelatine

1 µM of each of the primers;

200 µM of each of the dNTPs (dGTP, dATP, dTTP and dCTP).

After the addition of a paraffin pearl (Ampliwax™PCR Gem 100®-Perkin-Elmer Cetus) and denaturation for 4 minutes at 94° C., the program was started, which comprises:

1 minute at 94° C;.

1 minute at 42° C;.

1 minute at 72° C. (extension) for three cycles;

1 minute at 94° C. (denaturation);

1 minute at 55° C. (annealing);

1 minute at 72° C. for 30 cycles (extension);

8 minutes at 72° C. (final extension) for 30 cycles.

The amplification product thus obtained was precipitated with 3M Na-acetate pH 5.2 (1/10 volume) and Ethanol (2 volumes), resuspended in 40 µl of water and digested with the restriction enzymes NaeI and HindIII (Boehringer). The resulting mixture was charged on acrylamide gel 10% and run at 100 volts for 2 hours. The 240 bp band, comprising the DNA fragment containing the 3' terminal of the D-N-α-carbamoylase gene fused to the polyHis sequence, was cut away from the gel and the DNA eluated in 300 µl of water for 16 hours at 37° C. After precipitation the DNA was resuspended in 15 µl of TE (10 mM Tris-HCl pH 7.4, 1 mM EDTA).

The plasmid pSM637 (40 µg) was digested with the restriction enzymes NaeI and HindIII and resuspended in 200 µl of buffer for the sucrose gradients (30 mM Tris-HCl pH8, 10 mM EDTA and 1M NaCl) to remove the DNA fragment containing the 3' terminal region of the carbamoylase gene. The gradients were prepared, using solutions at 5% and 20% of sucrose in the buffer, with a gradient shaper (Buckler Auto Densi-Flow IIC). The total volume of the gradient was 16 ml. The sample was applied to the surface of the gradients and run for 20 hours in the SW28® rotor at 25,000 rpm, at a temperature of 20° C., in an ultracentrifuge L8-M (Beckman). The gradient was subsequently fractionated removing 40 fractions of 400 µl each from the surface. A tenth of the volume of each fraction was charged onto agarose gel and the fractions containing the single vector derived from pSM637 were collected separately. These fractions were then diluted 1:1 with $H_2O$ and precipitated from EtOH (2–3 volumes).

After resuspending the fragments in $H_2O$, a ligase reaction was carried out using the vector pSM637 (50 ng) and the fragment NaeI-HindIII of 220 bp (5 ng) obtained as described in example 1. The reaction was carried out in 10 µl of reaction mixture containing 66 mM Tris-HCl pH 7.6, 1 mM ATP, 10 mM $MgCl_2$, 10 mM dithiotreitol (DTT), in the presence of 1 U of T4 DNA ligase, at 16° C. for 16 hours.

An aliquot (2 µl) of this mixture was used to transform cells of E.coli 71/18 (BRL) made competent with 50 mM $CaCl_2$ (Dagert, M. and Ehrlich (1979), Gene, 6:23). The transformants were selected on plates of LB agar medium (0.8% Bacto triptone, 0.5% yeast Extract, 0.5% NaCl, agar 18 g/l) containing 20 µg/ml of chloramphenicol.

The plasmid DNA extracted from one of the positive Cm® clones (choramphenicol resistant), was sequenced using the Kit Sequenase® version 2.0 (United States Biochemical) to verify the presence of the polyHis tail at the 3' end of the carbamoylase gene. The plasmid thus obtained was called pSM716. The E.coli strain containing this plasmid was called SMC329.

EXAMPLE 2

Construction and screening of a mutant bank of the gene of D-N-α-carbamoylase

The mutagenesis was carried out by PCR under conditions in which an increase in the error frequency is produced during polymerization (Leung D. W. et al., 1989, Technique, 1, 11–15).

The following pair of oligonucleotides was used for the amplification:

a) 5'CTC GGC TTC CCG GTC TAT GAC GTC GAC3' (forward)(SEQ ID NO:7).

b) 5'GGC TTA CTT GTC TGC TTT C 3' (reverse)(SEQ ID NO.8).

The amplification was carried out in a DNA Thermal Cycler® 480 (Perkin-Elmer Cetus) using a reaction mixture (100 µl) containing:

1 ng of the plasmid pSM716;

84 picomoles (pmoles) of each oligonucleotide;

16.6 mM $(NH_4)_2SO_4$;

67 mM Tris-HCl pH 8.8;

6.1 mM $MgCl_2$;

6.7 mM EDTA pH 8;

0.17 mg/ml BSA;

10 mM of β-mercaptoethanol prepared on the spot;

10% of DMSO (v/v);

0.5 mM $MnCl_2$;

0.2 mM dATP, 1 mM dGTP, 1 mM dTTP and 1 mM dCTP.

The mixture was subjected to denaturation at 94° C. for 7 minutes and annealing of the primers at 50° C. for 1 minute. After adding the enzyme Taq DNA polymerase (Boehringer, 5 U/µl) and a paraffin pearl, the cyclic program was started, which comprises:

1 minute at 94° C. (denaturation);

1 minute at 50° C. (annealing);

4 minutes at 70° C. (extension) for a total of 25 cycles.

The amplification product of about 500 bp was precipitated with 7.5 M $NH_4$Acetate (0.6 volumes) and ethanol (2 volumes) and resuspended in 40 µl of $H_2O$. After digestion with the restriction enzymes SalI and HindIII the mutagenized fragment was purified on low-melting agarose gel at 0.8% (Nusieve, FMC Bioproducts). The band of interest was cut away, put at 68° C. for 15 minutes and treated with GELase® (Epicentre Technologies) (1 U for every 300 mg of gel weighed) for 1.5 hours at 45° C.

Parallelly, the plasmid pSM637 (30 µg) was digested with the restriction enzymes SalI and HindIII, precipitated with Na-acetate and ethanol, resuspended in 200 µl of buffer (30 mM Tris-HCl pH 8, 10 mM EDTA, 1 m NaCl) and purified by sucrose gradient operating as described in example 1. The fractions containing the plasmid were combined, diluted 1:1 with water, precipitated with ethanol (2–3 volumes) and resuspended in TE buffer.

500 ng of the purified plasmid pSM637 were ligated with the mutagenized fragment in 80 μl of ligase mixture at 16° C. for 14 hours.

An aliquot (1 μl) of the ligase mixture was used to transform cells of E.coli 71/18 (BRL) made competent by electroporation (Dower W. J., Miller J. F. and Ragsdale C. W., N. A. R. (1988), 16, 6127). The cells were then plated on LB medium (10 g/l Bacto-Tryptone® (DIFCO), 5 g/l Yeast Extract, 5 g/l NaCl, 300 μl NaOH 10N, 20 μg/ml chloramphenicol) and cultured at 37° C. for about 16 hours.

Replicas were made from each transformation plate on a nitrocellulose membrane (MFS, Sartorius). These replicas were subjected to three cycles of freezing-defreezing to lyse the colonies and subsequently placed at 48.5° C. for 16 hours.

After this inactivation treatment the membranes were transferred to plates containing 20 mM $C_DPG$ (carbamoyl of D-phenyl-glycine) in 20 mM of sodium phosphate buffer pH 7, 1% agarose (BioRad), 0.0032% of red phenol and incubated at 37°–40° C. After a few hours the colonies containing thermostable carbamoylase activity had a red-purple colouring, whereas the wild-type colonies no longer had any activity. The positive control of the test consisted in repeating the same procedure omitting the incubation at 48.5° C.; under these conditions the wild-type colonies had a red-purple colouring after a few minutes.

With this screening three thermostable clones SMC341, SMC342 and SMC343 were isolated. The plasmid DNA extracted from the clones was sequenced with Sequenase and, the mutations, shown in table 1, were identified for each clone:

TABLE 1

| Clone | Plasmid | Mutation |
|-------|---------|----------|
| SMC341 | pSM754 | Met184Leu and Phe304Ile |
| SMC342 | pSM755 | Thr212Ala |
| SMC343 | pSM756 | Thr262Ala |

EXAMPLE 3

Construction of single and multiple mutants

The mutations resulting to be thermostabilizing were introduced into the wild-type carbamoylase gene without the poly-His tail as single and multiple mutations.

The plasmid pSM637 (1 μg) was digested with 1 unit of the restriction enzymes EcoRI and HindIII (Boehringer) at 37° C. for 60 minutes. After blocking the enzymatic reaction at 65° C. for 10 minutes, the reaction mixture was charged onto low melting agarose gel at 0.8% and run at 50 volts for 2 hours. The EcoRI-HindIII band of 915 base pairs (bp), comprising the sequence encoding the D-N-α-carbamoylase, was then purified with Gelase® TM (Epicentre Technologics).

The fragment of DNA corresponding to this band (20 ng) was ligated to the vector M13mp8 (50 ng) previously digested with the same restriction enzymes. The ligase reaction was carried out in 20 μl of mixture containing 66 mM Tris-HCl pH 7.6, 1 mM ATP, 10 mM $MgCl_2$, 10 mM dithiotreitol (DTT), in the presence of 1 U of T4 DNA ligase, at 16° C. for 16 hours.

An aliquot (5 μl) of the ligase mixture was used to transform cells of E.coli 71/18 (BRL) made competent with 50 mM $CaCl_2$ (Dagert, M. and Ehrlich (1979), Gene, 6:23).

The transformants were then selected on plates of YT agar (8 g/l Bacto tryptone (DIFCO) 5 g/l NaCl) containing 40 μg/ml of X-Gal (5-bromo-4-chloro-4-indolyl-D-thio galactopyranoside) and 125 μg/ml of isopropyl-beta-D-thiogalacto-pyranoside (IPTG). Operating as described above, numerous positive recombinant plaques (white) were obtained which could be easily distinguished from those non-recombinant (blue).

The single-stranded (SS) bacteriophage DNA to be used as template in the specific site mutagenesis phase, was prepared from one of the positive plaques which showed the exact insertion.

The following oligonucleotides were synthesized to introduce the desired mutations:

(1) 5' GCC CTT AAG TCC CAA CAC CCG CCA' CGT 3' (SEQ ID NO:9) inserts the mutation Met184→Leu;

(2) 5' GTG GTG GAA GGA CGC CAG ATG GTC GTG 3' (SEQ ID NO:10) inserts the mutation Thr212→Ala;

(3) 5' TTC CAA CGT CGT GGCCAG GGC AAC GAT 3' (SEQ ID NO:11) inserts the mutation Thr262→Ala;

(4) 5' AAG CTT CAA ATT TCC GCG ATC AG 3' (SEQ ID NO:12) inserts the mutation Phe304→Ile;

These oligonucleotides were phosphorylated at the 5'-end in 30 μl of reaction mixture containing 100 mM Tris-HCl pH 8, 10 mM $MgCl_2$, 5 mM DTT, 1 mM ATP and 2 U of T4 polynucleotide Kinase (promega), by incubation at 37° C. for 30 minutes. The phosphorylated oligonucleotides were then used alone and combined in the mutagenesis reactions in vitro using the kit "Sculptor® in vitro mutagenesis System" (Amersham).

Some of the plaques obtained were used for infecting cultures of E.coli TG1 (Amersham) and the single-stranded (ssDNA) and double-stranded (RF, dsDNA) bacteriophagic DNAs were subsequently extracted from each culture.

The ssDNAs were sequenced with the kit "Sequenase® 2.0" (United States Biochemical) based on the method described by Sanger et al. (PNAS) (1977) 74: 5463) to verify the presence of the desired mutation. The corresponding dsDNAs were used to subclone the modified genes in the plasmid pSM671 CBS 205.94.

EXAMPLE 4

Subcloning the mutants in the plasmid pSM671

The plasmid pSM671 (1 μg) was digested with the restriction enzymes EcoRI and HindIII in a final volume of 20 μl. parallelly the mutant bacteriophage DNAs in replicative form were digested separately with the restriction enzymes EcoRI and HindIII in a final volume of 20 μl. The modified genes, obtained as fragments of about 920 bp, were then subcloned by ligating an aliquot of the digestion mixture (5 μl) with about 50 ng of digested pSM671. The ligase mixtures were used to transform cells of E.coli 71/18 electrocompetent and the transformants were selected on plates of LB containing 20 μg/ml of Chloramphenicol. The plasmid DNA extracted from positive clones was rechecked by sequencing. The plasmids containing the modified genes are shown in table 2.

TABLE 2

| Clone | Plasmid | Mutation |
|-------|---------|----------|
| SMC344 | pSM758 | Met184Leu |
| SMC345 | pSM759 | Thr212Ala |
| SMC346 | pSM760 | Thr262Ala |
| SMC347 | pSM761 | Met184Leu-Thr212Ala |
| SMC348 | pSM762 | Met184Leu-Thr212Ala-Thr262Ala |
| SMC349 | pSM763 | Thr212Ala-Thr262Ala-Phe304Ile |
| SMC350 | pSM764 | Met184Leu-Thr212Ala-Thr262Ala-Phe30- |

TABLE 2-continued

| Clone | Plasmid | Mutation |
|---|---|---|
| | | 4Ile |
| SMC351 | pSM765 | Thr262Ala-Phe304Ile |
| SMC3S6 | pSM770 | Met184Leu-Thr262Ala |
| SMC357 | pSM771 | Thr212Ala-Thr262Ala |

EXAMPLE 5

Expression of mutant clones

Single colonies of mutant clones were inoculated in 50 ml flasks each containing 5 ml of LB medium to which 20 μg/ml of chloramphenicol had been added and incubated, under stirring (200 rpm), at 37° C. for 16 hours ($DO_{600}$ about 4). As a control, the strain of E. coli containing the plasmid pSM716 carrying the wild-type carbamoylase gene fused to the histidine tail was cultured under the same conditions described above.

The cultures were then centrifuged at 12000 rpm for 1 minute (SJ14® rotor, Beckman). The cells thus recovered were resuspended in 300 μl of lysis buffer 20 mM $NaPO_4$, 20% glycerol and lysed by sonication (Soniprep®150, MSE impulses of 1 minute, at medium voltage). An aliquot (20 μl) of each lysate was analyzed by SDS-PAGE 10%. Electrophoretic analysis showed for all the enzymes comparable expression levels with respect to each other and to the wild-type enzyme.

EXAMPLE 6

Study of the thermostability of the modified enzymes

The thermostability of the mutants was studied using the technique which involves the heating of various aliquots of soluble cellular extracts, obtained in a lysis buffer without glycerol, at different temperatures and subsequent calculation of the residual activity on carbamoyl of D-phenylglycine ($C_DPG$).

In practice the cellular extracts were appropriately diluted in 20 mM phosphate buffer pH 7 and aliquots (100 μl) of these, each containing an equal enzymatic activity, were incubated at temperatures of between 50 and 80° C. for 30 minutes. The positive control was kept in ice.

500 μl of a solution of carbamoyl of D-phenylgly-cine ($C_DPG$) 0.12M, in phosphate buffer 0.2M, pH7 were subsequently added to 50 μl of each cellular extract and positive control to determine the residual enzymatic activity. The activity value considered as 100% was determined on an aliquot not subjected to thermal treatment.

From the inactivation curves thus obtained the $T_{50}$ value, defined as the temperature at which 50% of the enzyme is inactivated, was calculated. The results are shown in FIG. 1 where: ■ wild-type strain; + mutant 184; * mutant 212; ⊟ mutant 262; ✕ mutant 184-212; ◆ mutant 184-262; ▲ mutant 212-262; ✕ mutant 184-212-262.

Table 3 shows the $T_{50}$ values, calculated as an average of the various experiments carried out for each sample, and the $\Delta T_{50}$ values; the variability for each datum provided is between ±0.1° and ±0.3° C.

TABLE 3

| Carbamoylase mutants | $T_{50}$ (C.°) | $\Delta T_{50}$ °C. |
|---|---|---|
| wild-type | 61 | — |
| Met184Leu | 62.6 | 1.6 |
| Thr212Ala | 65.8 | 4.8 |

TABLE 3-continued

| Carbamoylase mutants | $T_{50}$ (C.°) | $\Delta T_{50}$ °C. |
|---|---|---|
| Thr262Ala | 70 | 9.0 |
| Thr262Ala-Phe304Ile | 69 | 8.0 |
| Met184Leu-Thr212Ala | 73.8 | 12.8 |
| Met184Leu-Thr262Ala | 70.2 | 9.2 |
| Thr212Ala-Thr262Ala | 74 | 13 |
| Met184Leu-Thr212Ala-Thr262Ala | 73.8 | 12.8 |
| Thr212Ala-Thr262Ala-Phe304Ile | 72.4 | 11.4 |
| Met184Leu-Thr212Ala-Thr262Ala-Phe304Ile | 73.1 | 12.1 |

These results clearly show that the substitution of one or more amino acid residues increases the thermal stability of the carbamoylase.

EXAMPLE 7 (comparative)

Some of the mutants prepared as described in the previous examples were compared with the mutants of the known art (EP-610517) prepared by specific-site mutagenesis using the following oligonucleotides:
1) 5'GTC GGT GAA ATA CCA CCG CGG GAA 3' (SEQ ID NO:13) which inserts the mutation His58→Tyr
2) 5'CGT CAG ATG ATC ATG CTG GGG AAC TTC GGG ATT GTG 3' (SEQ ID NO:14) which inserts the mutation Pro204→Glu
3) 5'CAG CAT GCA TCC CTC CTC CAT GCC AGC CTT GCC GCC 3' (SEQ ID NO:15) which inserts the mutation Val237→Ala.

The numbering takes into account the initial Methionine (Met) of the carbamoylase.

The subcloning was carried out in the plasmid pSM671 operating as described in example 4. The clones containing the desired mutations were identified and analyzed as a comparison with the mutants of the present invention which proved to be more thermostable.

An equal quantity of the cells of the wild-type clone and mutants listed in table 4 was resuspended in 500 μl of buffer containing 20 mM $NaPO_4$ pH7 and glycerol 20% and sonicated. The soluble cellular extracts obtained were analyzed by means the activity test and electrophoretic analysis. The results are shown in table 4 and in FIG. 2 respectively wherein: line 1 and 9 standard carbamoylase; line 2 w.t. carbamoylase; line 3 mutant 184-212; line 4 mutant line 5 mutant 212-262; line 6 mutant 184-212-262; line 7 mutant 58-237 and line 8 mutant 58-204-237. Table 4 shows the activity data expressed in U/ml and U/mg of soluble proteins.

TABLE 4

| | ACTIVITY | |
|---|---|---|
| MUTANTS | U/ml | U/mg |
| wild-type | 1.25 | 0.64 |
| Met184Leu-Thr212Ala | 1.71 | 0.83 |
| Met184Leu-Thr262Ala | 2.00 | 1.01 |
| Thr212Ala-Thr262Ala | 1.58 | 0.83 |
| Met184Leu-Thr212Ala-Thr262Ala | 1.62 | 0.89 |
| His58Tyr-Val237Ala | 0.63 | 0.36 |
| His58Tyr-Pro204Glu-Val237Ala | 0.82 | 0.45 |

EXAMLE 8

Construction of operon expression systems regulated by a single promoter

The genes of the more thermostable mutants were linked in tandem with the wild-type hydantoinase gene to construct operon expression systems regulated by a single promoter.

About 1 μg of the plasmids pSM761, pSM762, pSM763 and pSM764 were digested with the restriction enzymes HindIII and PstI, precipitated with Na-acetate and ethanol and the DNAs resuspended in 20 μl of TE buffer.

The plasmid pSM700 (6 μg) CBS 668.95, containing the carbamoylase-hydantoinase operon, was digested with the restriction enzymes HindIII and PstI and charged on low-melting agarose gel 0.8%. The band of about 1400 bp, corresponding to the hydantoinase gene preceded by its RBS sequence, was cut away and the DNA extracted by "freeze-squeeze" (Anal.Biochem., 132: 14, 1983).

In this method the band is first balanced for 5–10 minutes in an excess of buffer 0.3M Na-acetate, 1 mM EDTA, pH 7.1, then removed and charged into a 0.5 ml eppendorf test-tube, perforated on the bottom containing a flock of silicon glass wool. The test-tube is subsequently inserted into a 1.5 ml eppendorm test-tube. This is then frozen for 20 minutes at −80° C. and immediately afterwards centrifuged in a microcentrifuge for 15 minutes at room temperature. The eluated DNA in the 1.5 ml test-tube is recovered and precipitated with ethanol, after the addition of 0.1% acetic acid and 10 mM $MgCl_2$ and finally resuspended in 20 μl of TE.

About 30 ng of the plasmids digested as described above were ligated with 5 μl of the fragment of about 1400 bp in a final volume of 10 μl. The ligase mixture was used to transform competent E.coli 71/18 and the transformants were selected on LB-chloramphenicol plates. The plasmid DNA extracted from the positive clones contained a fragment of about 2300 bp corresponding to the operon constructed from the mutant carbamoylase gene and the wild-type hydantoinase gene. Table 5 shows the clones and plasmids containing the operon.

TABLE 5

| Clone | Plasmid | mut.carbamoyl.-w.t.hydant.operon |
|---|---|---|
| SMC352 | pSM766 | Met184Leu-Thr212Ala-Thr262Ala-Phe304Ile |
| SMC353 | pSM767 | Met184Leu-Thr212Ala-Thr262Ala |
| SMC354 | pSM768 | Thr212Ala-Thr262Ala-Phe304Ile |
| SMC355 | pSM769 | Met184Leu-Thr212Ala |

EXAMPLE 9

Expression of the operons

Single colonies of the clones SMC352, 353, 354 and 355 were inoculated in 50 ml flasks each containing 5 ml of LB medium to which 20 μg/ml of chloramphenicol had been added and incubated at 37° C. for 16 hours ($DO_{600}$ about 4), under stirring (200 rpm).

As control, the strain of E.coli SMC327 containing the plasmid pSM700 carrying the wild-type carbamoylase gene fused to the hydantoinase gene was cultured under the same conditions.

The cultures were then centrifuged at 12000 rpm for 1 minute (SJ14® rotor, Beckman) and the cells thus obtained were resuspended in 300 μl of lysis buffer 20 mM $NaPO_4$, 20% glycerol and lysed by sonication (Soniprep150, MSE 1 minute impulses, at medium voltage). 20 μl of each lysate were analyzed by SDS-PAGE 10%. Electrophoretic analysis showed that all the enzymes were expressed in comparable quantities with respect to each other and to the expression level of the wild-type operon.

B) Determination of the enzymatic activities

Flasks containing 50 ml of LB medium to which choramphenicol (20 μg/ml) had been added were inoculated with precultures of the clones SMC327 and SMC355 and incubated at room temperature until an optical density $DO_{600}$ of about 4. Subsequently, equal quantities of cells were removed, resuspended in buffer 0.2M $NaPO_4$ pH 8.5 and sonicated. The soluble fractions were recovered by centrifugation and used for the dosing of the hydantoinase activity, which results from the sum of the quantity of carbamoyl and amino acid produced, and the carbamoylase activity.

The hydantoinase activity test was carried out at 40° C. by adding 100 μl of cellular extract to 3.5 ml of buffer $NaPO_4$ 0.2 M pH 8.0 containing D,L-p-hydroxyphenyl hydantoin 20 mM. At intervals of time aliquots (0.6 ml) of the reaction mixture were removed and immediately treated with 0.2 ml of trichloroacetic acid at 15% in water. The precipitated proteins were removed by centrifugation and 0.25 ml of Ehrlich reagent (10% 4dimethylaminobenzaldehyde in concentrated HCl) were added to 0.5 ml of surnatant for the calorimetric determination at 438 nm of the carbamoyl formed. Parallelly, the content of amino acid was calorimetrically determined at 625 nm on an aliquot (50 μl) of the reaction mixture using the Berthelot reagent according to the procedure of Weatherburn, M. W. (Anal. Chem., vol. 39, 971, 1967).

Enzymatic unit defines the quantity of enzyme which hydrolyzes a micromole of hydantoin in a minute at 40° C. under the test conditions described above.

The carbamoylase activity was determined at 40° C. in 0.5 ml of buffer $NaPO_4$ 0.2M pH 7.0 containing D-carbamoyl-p-hydroxyphenyl glycine 0.12M. The content of amino acid was determined at different reaction times by removing 50 μl of the reaction mixture and operating as described above.

Enzymatic unit defines the quantity of enzyme which hydrolyzes a micromole of carbamoyl in a minute at 40° C. under the above test conditions. The results are shown in table 6 below.

TABLE 6

| Strain | Proteins (mg/ml) | Carbamoylase (U/mg) | Carbamoylase (U/ml) | Hydantoinase (U/mg) | Hydantoinase (U/ml) |
|---|---|---|---|---|---|
| SMC327 (pSM700) | 28.42 | 13.18 | 0.46 | 1.92 | 0.07 |
| MC355 (pSM769) | 22.63 | 17.46 | 0.77 | 2.25 | 0.1 |

From the results shown in the table it can be seen that in the clones containing the double mutation in the carbamoylase gene there is not only an increase in the thermal stability but also an improvement in the carbamoylase and hydantoinase activity.

We claim:

1. Thermostable mutants of *Agrobatorium Radiobactor* D-N-α-carbamoylase characterized in that, at least one of the amino acid residues Met184, Thr212, Thr262 and phe304 of the amino acid sequence of wild-type D-N-α-carbamoylase is substituted with a different residue selected from the group of natural amino acids.

2. A thermostable mutant of D-N-α-carbamoylase according to claim 1, characterized in that the amino acid residue Met184 is substituted with L-Leucine.

3. A mutant of D-N-α-carbamoylase according to claim 1, characterized in that the amino acid residue Phe304 is substituted with L-Isoleucine.

4. A mutant of D-N-α-carbamoylase according to claim 1, characterized in that the amino acid residue Thr212 is substituted with L-Alanine.

5. A mutant of D-N-α-carbamoylase according to claim 1, characterized in that the amino acid residue Thr262 is substituted with L-alanine.

6. A mutant of D-N-α-carbamoylase according to claim 1, characterized in that the amino acid residues Met184 and Phe304 are both substituted with an amino acid residue.

7. A mutant of D-N-α-carbamoylase according to claim 1, characterized in that the amino acid residues Met184 and Thr212 are both substituted with an amino acid residue.

* * * * *